(12) United States Patent
Varadhachary et al.

(10) Patent No.: US 7,638,487 B2
(45) Date of Patent: Dec. 29, 2009

(54) LACTOFERRIN IN THE REDUCTION OF PAIN

(75) Inventors: Atul Varadhachary, Houston, TX (US); Karel Petrak, Houston, TX (US)

(73) Assignee: Agennix, Inc., Houston, TX (US)

( * ) Notice: Subject to any disclaimer, the term of this patent is extended or adjusted under 35 U.S.C. 154(b) by 0 days.

(21) Appl. No.: 11/947,345

(22) Filed: Nov. 29, 2007

(65) Prior Publication Data

US 2008/0070833 A1 Mar. 20, 2008

Related U.S. Application Data

(63) Continuation of application No. 10/733,621, filed on Dec. 11, 2003, now Pat. No. 7,323,443.

(60) Provisional application No. 60/432,937, filed on Dec. 12, 2002, provisional application No. 60/498,248, filed on Aug. 27, 2003.

(51) Int. Cl.
*A61K 38/00* (2006.01)
*A61K 38/40* (2006.01)

(52) U.S. Cl. .............................. 514/6; 514/8; 530/350; 530/395; 530/400; 424/9.1; 424/85.1

(58) Field of Classification Search .................. 514/8, 514/6; 530/350, 395, 400; 424/85.1, 9.1
See application file for complete search history.

(56) References Cited

U.S. PATENT DOCUMENTS

| | | | |
|---|---|---|---|
| 5,561,109 | A | 10/1996 | Mita et al. |
| 5,576,299 | A | 11/1996 | Ando et al. |
| 5,712,247 | A | 1/1998 | Wu et al. |
| 5,919,913 | A | 7/1999 | Nuyens et al. |
| 6,066,469 | A | 5/2000 | Kruzel et al. |
| 6,080,559 | A | 6/2000 | Conneely et al. |
| 6,100,054 | A | 8/2000 | Conneely et al. |
| 6,228,614 | B1 | 5/2001 | Conneely et al. |
| 6,277,817 | B1 | 8/2001 | Kruzel et al. |
| 6,333,311 | B1 | 12/2001 | Nuijens et al. |
| 6,455,687 | B1 | 9/2002 | Kruzel et al. |
| 2002/0064524 | A1 | 5/2002 | Cevc |
| 2002/0107283 | A1 | 8/2002 | Codd et al. |
| 2003/0039651 | A1 | 2/2003 | Olmarker |
| 2003/0077641 | A1 | 4/2003 | Laskowitz et al. |
| 2003/0096763 | A1 | 5/2003 | Or et al. |
| 2004/0009895 | A1 | 1/2004 | Varadhachary et al. |
| 2004/0018190 | A1 | 1/2004 | Ando et al. |
| 2005/0019342 | A1 | 1/2005 | Varadhachary et al. |

FOREIGN PATENT DOCUMENTS

| | | |
|---|---|---|
| WO | WO-98/33509 | 8/1998 |
| WO | WO-00/01730 | 1/2000 |
| WO | WO-02/03910 | 1/2002 |
| WO | WO-02080897 | 10/2002 |
| WO | WO-03/061688 | 7/2003 |

OTHER PUBLICATIONS

Baraniuk et al, "Hypertonic Saline Nasal Provocation Stimulates Nociceptive Nerves, Substance P Release, and Glandular Mucous Exocytosis in Normal Humans," Am J Respir Crit care Med vol. 160, 1999, pp. 655-662.
Brink, "Lactoferrin: The Bioactive Peptide that Fights Disease," *Life Extension Magazine*, found at http://www.lef.org/LEFCMS/aspx/PringVersionMagic.aspx?CmsID=31812, Oct. 2000.
Eckmann, L. "Mucosal defences against Giardia," Parasite Immunol. vol. 25 No. 5, May 2003, pp. 259-270.
Hayashida et al, "Lactoferrin enhances opioid-mediated analgesia via nitric oxide in the rat spinal cord," Am J Physiol Regul Integr Comp Physiol 285, 2003; R306-R312.
Hayashida et al, "Novel function of bovine milk-derived lactoferrin on antinociception mediated by M-opioid receptor in the rat spinal cord," Brain research 965, 2003, pp. 239-245.
Teschemacher, Hansjorg "Lactoferrin elicits opioid-mediated antinociception without development of toleence: central nNOS-1 set off duty?" American Journal Physiol. Regul Integr Comp Physiol 285, 2003, R302-R305.
Ho, R.C.S., "Pain in the Cancer Patient," Ca Cancer J Clin, 1994: 44, 259-261.
Mercadante, S. "Pain treatment and outcomes for patients with advanced cancer who receive home follow-up care at home." Cancer, Apr. 15, 1999: 85 (8):1849-1858.
Griffin et al., On the receiving end V: Patients perceptions of the side effects of cancer chemotherapy in 1993, Annals of Oncology 7: 189-195, 1996.

*Primary Examiner*—Chih-Min Kam
(74) *Attorney, Agent, or Firm*—Fulbright & Jaworski L.L.P.

(57) ABSTRACT

The present invention relates to methods of using lactoferrin (LF) to reduce pain in conditions associated with severe or intractable pain by administering a composition of lactoferrin either alone or in combination with other therapy for pain.

12 Claims, 2 Drawing Sheets

LACTOFERRIN IN THE REDUCTION OF PAIN

CROSS-REFERENCE TO RELATED APPLICATIONS

This application is a continuation of U.S. application Ser. No. 10/733,621, filed Dec. 11, 2003, now U.S. Pat. No. 7,323,443, which claims priority to U.S. Provisional Application Nos. 60/432,937 filed Dec. 12, 2002 and 60/498,248 filed Aug. 27, 2003, which are incorporated herein by reference.

TECHNICAL FIELD

The present invention relates to methods of using lactoferrin (LF) to reduce pain in conditions associated with severe or intractable pain by administering a composition of lactoferrin.

BACKGROUND OF THE INVENTION

Pain is one of the most common medical conditions requiring interventions with 25 million people in the US suffering from chronic pain alone and chronic pain management costing $65 Billion annually. Pain can be the result of a large number of medical conditions and can range in severity from mild to intractable. Despite a broad range of therapeutic and non-therapeutic interventions, there is still a large unmet need for effective and safe pain medications.

Lactoferrin is a single-chain metal binding glycoprotein. Many cell types, such as monocytes, macrophages, lymphocytes, and brush-border cells in the intestine, are known to have lactoferrin receptors. Lactoferrin is found mainly in external secretions of mucosal epithelia such as breast milk, saliva, tears, bile, and pancreatic fluid and has a wide array of functions related to host primary defense mechanisms. For example, lactoferrin has been reported to activate natural killer (NK) cells, induce colony-stimulating activity, activate polymorphonuclear neutrophils (PMN), regulate granulopoeisis, enhance antibody-dependent cell cytotoxicity, stimulate lymphokine-activated killer (LAK) cell activity, and potentiate macrophage toxicity.

Recombinant human lactoferrin has previously been described as being purified after expression in a variety of prokaryotic and eukaryotic organisms including aspergillus (U.S. Pat. No. 6,080,559), cattle (U.S. Pat. No. 5,919,913), rice, corn, Sacharomcyes (U.S. Pat. No. 6,228,614) and Pichia pastoris (U.S. Pat. No. 6,455,687, U.S. Pat. No. 6,277,817, U.S. Pat. No. 6,066,469). Also described are expression systems for the expression of full-length human lactoferrins (e.g., U.S. Pat. No. 6,100,054). In all cases, part of the teaching is expression of the full-length cDNA and purification of the intact protein whose N-terminal amino acid is, after processing of the leader peptide, the amino acid glycine. Nuijens et al. (U.S. Pat. No. 6,333,311) separately describe variants of human lactoferrin but their focus is limited to deletion or substitution of arginine residues found in the N-terminal domain of lactoferrin.

The present invention is the first to use a lactoferrin composition as a means of reducing or eliminating pain associated with a broad range of medical conditions.

BRIEF SUMMARY OF THE INVENTION

The present invention is directed to a method of administering a lactoferrin composition, either alone or in combination with other therapies, for the reduction of acute or chronic pain.

The lactoferrin composition, which is dispersed in a pharmaceutically acceptable carrier, comprises lactoferrin or an N-terminal lactoferrin variant in which at least the N-terminal glycine residue is truncated or substituted. The lactoferrin is mammalian lactoferrin, more particularly, the lactoferrin is human or bovine. Yet further, the lactoferrin is recombinant lactoferrin. In specific embodiments, the N-terminal lactoferrin variant comprises at least 1% of the lactoferrin composition, at least 5% of the lactoferrin composition, at least 10% of the lactoferrin composition, at least 25% of the lactoferrin composition, at least 50% of the lactoferrin composition or any range in between.

The amount of the lactoferrin that is administered is about 1 ng to about 100 g per day, more preferably, the amount is about 0.1 g to about 10 g per day. More particularly, the composition is a topical gel, a solution, capsule or a tablet having a lactoferrin concentration of about 0.1% to about 100%.

In further embodiments, a metal chelator dispersed in a pharmaceutically acceptable carrier can also be administered with the lactoferrin composition. Preferred metal chelator include, but are not limited to ethylenediaminetetraacetic acid (EDTA) or [ethylenebis(oxyethylenenitrilo)]tetraacetic acid (EGTA). More preferably, the metal chelator is EDTA. The amount of EDTA that is administered is about 1 ng to about 1 g per day.

An embodiment of the present invention is method of treating a subject suffering from pain comprising the step of administering to the subject an effective amount of a lactoferrin composition to provide an improvement in pain in the subject. The pain is acute or chronic pain. The lactoferrin composition reduces the severity of the patient's pain.

The lactoferrin composition can be administered orally, parenterally or topically. In a further embodiment, the lactoferrin composition is administered orally. For oral administration, an antacid in combination with the lactoferrin composition can be administered. The lactoferrin can be formulated in a delayed release formulation. Still further, the lactoferrin composition can be formulated wherein release occurs in the small intestine or in the large intestine.

The lactoferrin composition reduces the production or activity of pro-inflammatory cytokines or enhances the production or activity of cytokines, for example TNF-α.

A further embodiment comprises administering a lactoferrin composition in combination with a pharmacological agent used to relieve pain. The pharmacological agent is selected from the group consisting of non-steroidal anti-inflammatory drugs (NSAIDS), opioid analgesics, second-generation NSAIDs and anti-depressant drugs.

Still further, another embodiment comprises administering a lactoferrin composition in combination with a non-pharmacological pain management technique. The non-pharmacological pain management technique is selected from the group consisting of acupuncture, acupressure, local anesthesia, regional anesthesia (e.g., spinal anesthesia), general anesthesia (intravenous anesthetics or opioid pump) and chiropractic.

Another specific embodiment comprises administering a lactoferrin composition in combination with a non-approved, non-pharmacological pain-reduction agent. Exemplary non-pharmacological pain-reduction agents include, but are not limited to devil's claw, capsaicin, menthold or L-phenylalanine.

Another embodiment is a method of modulating acute pain in a subject comprising the step of administering to the subject a lactoferrin composition in an amount to provide an improvement in acute pain in the subject.

Yet further, another embodiment is a method of modulating chronic pain in a subject comprising the step of administering to the subject a lactoferrin composition in an amount to provide an improvement in chronic pain in the subject.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

DETAILED DESCRIPTION OF THE INVENTION

Figure 1:
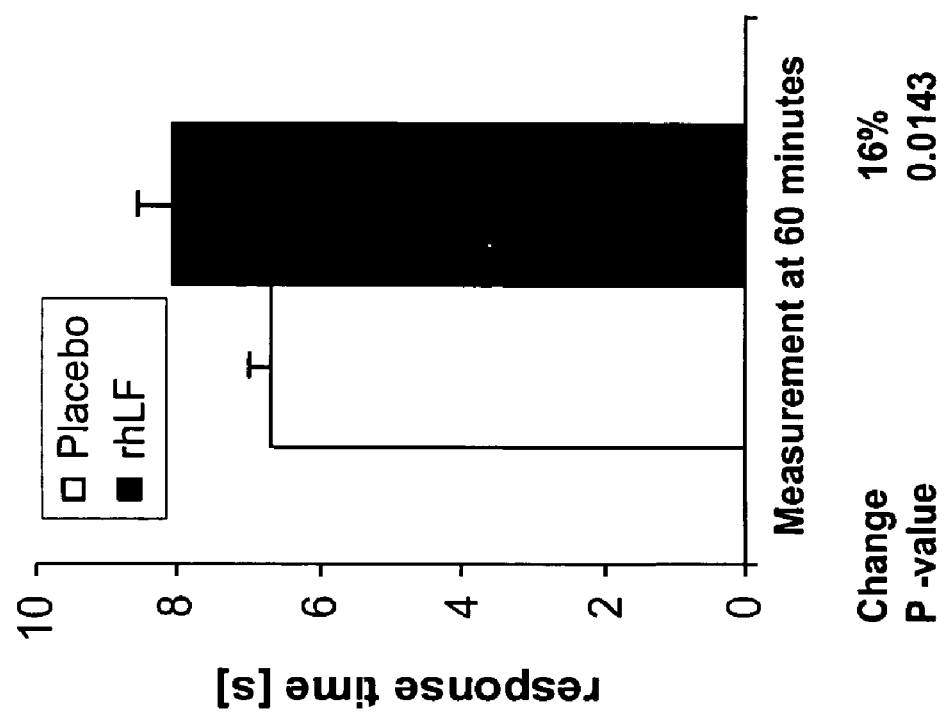
FIG. 1 shows reduction in heat-induced pain as measured by tail flick test in mice.

It is readily apparent to one skilled in the art that various embodiments and modifications can be made to the invention disclosed in this application without departing from the scope and spirit of the invention.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "containing", "including" and "comprising" are interchangeable and one of skill in the art is cognizant that these terms are open ended terms.

The term "acute pain" as used herein includes tissue injury or pathology. For example, acute pain includes, but is not limited to pain following surgery (e.g., surgery), pain following trauma (e.g., blunt or sharp injury, bullet wounds), pain associated with athletic injury, and the occasional headache. Medically, acute pain can have a diagnostic value; that is, it leads to the discovery of a pathological condition. Yet further, acute pain lasts or is anticipated to last for a short period of time, typically less than one to two months. Acute pain is associated with hyperactivity of the sympathetic nervous system, for example, tachycardia, increased respiratory rate, increased blood pressure, increased cortisol release, diaphoresis and dilated pupils.

The term "anti-depressant drugs" as used herein includes compounds that provide pain relief by reducing side-effects including anxiety. Anti-depressant drugs include, for example, but not limited to tricyclin antidepressants, sedatives, tranquilizers, hypnotics, anti-histamines, and amphetamines.

The term "chronic pain" as used herein refers to pain that lasts longer than 1 month or beyond the resolution of an acute tissue injury or is recurring or is associated with tissue injury and/or chronic diseases that are expected to continue or progress, for example, cancer, arthritis, inflammatory disease, chronic wounds, cardiovascular accidents, spinal cord disorders, central nervous system disorder or recovery from surgery. Chronic pain can be associated with several factors that include, but are not limited to lassitude, sleep disturbance, decreased appetite, loss of taste for food, weight loss, diminished libido, constipation, or depression.

The term "chemokine" as used herein refers to small proteins that are involved in stimulating or inhibiting the migration and activation of cells, for example phagocytic cells and lymphocytes. One of skill in the art realizes that chemokines play a central role in inflammatory and immune response processes.

The term "cytokine" as used herein refers to proteins that are made by cells that affect the behavior of other cells, for example stimulate or inhibit cell proliferation. For example, cytokines that are made by lymphocytes are often called lymphokines or interleukins. One of skill in the art realizes that the term cytokine is a generic term used in the literature to refer to proteins that are made by cells that can affect the behavior of other cells.

The term "effective amount" or "therapeutically effective amount" as used herein refers to an amount that results in an improvement or remediation of the symptoms of the disease or condition.

The term "lactoferrin" or "LF" as used herein refers to native or recombinant lactoferrin. Native lactoferrin can be obtained by purification from mammalian milk or colostrum or from other natural sources. Recombinant lactoferrin (rLF) can be made by recombinant expression or direct production in genetically altered animals, plants, fungi, bacteria, or other prokaryotic or eukaryotic species, or through chemical synthesis.

The term "lactoferrin composition" as used herein refers to a composition having lactoferrin, a portion or part of lactoferrin, an N-terminal lactoferrin variant, or a combination thereof.

The term "metal chelator" as used herein refers to a compound which binds metal. Metal chelators that can be used in the present invention include the divalent metal chelators, for example, ethylenediaminetetraacetic acid (EDTA), [ethylenebis(oxyethylenenitrilo)]tetraacetic acid (EGTA), 1,2-bis(2-aminophenoxy)ethane-N,N,N',N'-tetraacetic acid (BAPTA), hydroxyethylene diamine triacetic acid (HEDTA), or salts thereof.

The term "N-terminal lactoferrin variant" as used herein refers to lactoferrin wherein at least the N-terminal glycine has been truncated and/or substituted. N-terminal lactoferrin variants also include, but are not limited to deletion and/or substitution of one or more N-terminal amino acid residues, for example 1, 2, 3, 4, 5, 6, 7, 8, 9, 10, 11, 12, 13, 14, 15, or 16 N-terminal amino acid residues, etc. Thus, N-terminal lactoferrin variants comprise at least deletions or truncations and/or substitutions of 1 to 16 N-terminal amino acid residues. The deletion and/or substitution of at least the N-terminal glycine of lactoferrin mediates the same biological effects as full-length lactoferrin and/or may enhance lactoferrin's biological activity, for example by stimulating the production of various cytokines (e.g., IL-18, MIP-3α, GM-CSF or IFN-γ) by inhibiting various cytokines, (e.g., IL-2, IL-4, IL-5, IL-6, IL-10, and TNF-α), thus modulating acute or chronic pain.

The term "non-steroidal anti-inflammatory drugs" or "NSAIDs" as used herein includes compounds that are prescribed for mild to moderate pain and typically work by decreasing inflammation at the site of tissue injury. NSAIDs include, for example, but are not limited to aspirin, indomethacin, ibuprofen, naproxen, acetaminophen, and ketoprofen.

The term "opioid analgesics" as used herein include compounds that are prescribed to alleviate moderate to severe chronic pain or acute pain or mild to moderate pain and. Opioid analgesics include, for example, but are not limited to codeine, morphine, methadone, demerol, fentanyl, oxymorphone, and levarphanol.

The term "oral administration" as used herein includes oral, buccal, enteral or intragastric administration.

The term "parenteral administration" as used herein includes any form of administration in which the compound is absorbed into the subject without involving absorption via the intestines. Exemplary parenteral administrations that are used in the present invention include, but are not limited to intramuscular, intravenous, intraperitoneal, intraocular, subcutaneous or intraarticular administration. Yet further, parenteral administration also includes administration into a surgical field.

The term "pain" as used herein refers to an unpleasant sensation. For example, the subject experiences discomfort, distress or suffering. Pain of a moderate or high intensity is typically accompanied by anxiety. Thus, one of skill in the art is cognizant that pain may have dual properties, for example sensation and emotion.

The term "pharmaceutically acceptable carrier" as used herein includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The term "second-generation NSAIDs" as used herein includes compounds that are prescribed for mild to moderate pain and typically work by decreasing inflammation at the site of tissue injury with less gastrointestinal adverse effects. Second-generation NSAIDs include, for example, but are not limited to Cox-2 inhibitors such as Celebrex® and Vioxx®.

The term "subject" as used herein, is taken to mean any mammalian subject to which a human lactoferrin composition is administered according to the methods described herein. Thus, a skilled artisan realizes that a mammalian subject, includes, but is not limited to humans, monkeys, horses, pigs, cows, dogs, cats, rats and mice. In a specific embodiment, the methods of the present invention are employed to treat a human subject.

The term "topical administration" as used herein includes, but is not limited to topical, dermal, epidermal, oro-pharyngeal cavity, vaginal, rectal, or perineum.

The term "treating" and "treatment" as used herein refers to administering to a subject a therapeutically effective amount of a recombinant human lactoferrin composition so that the subject has an improvement in the parameters relating to pain. The improvement is any observable or measurable improvement including subjective or objective measures of pain or the use of additional or concurrent pain medication. Thus, one of skill in the art realizes that a treatment may improve the patient condition, but may not be a complete cure of the disease.

A. LACTOFERRIN

The lactoferrin used according to the present invention can be obtained through isolation and purification from natural sources, for example, but not limited to mammalian milk. The lactoferrin is preferably mammalian lactoferrin, such as bovine or human lactoferrin. In preferred embodiments, the lactoferrin is produced recombinantly using genetic engineering techniques well known and used in the art, such as recombinant expression or direct production in genetically altered animals, plants or eukaryotes, or chemical synthesis. See, e.g., U.S. Pat. Nos. 5,571,896; 5,571,697 and 5,571,691, which are herein incorporated by reference.

In certain aspects, the present invention provides lactoferrin variants having enhanced biological activities over natural LF and or rLF, e.g., the ability to stimulate and/or inhibit cytokines or chemokines. In particular, the invention provides variants of lactoferrin from which at least the N-terminal glycine residue has been substituted and/or truncated. The N-terminal lactoferrin variants may occur naturally or may be modified by the substitution or deletion of one or more amino acids.

The deletional variants can be produced by proteolysis of lactoferrin and/or expression of a polynucleotide encoding a truncated lactoferrin as described in U.S. Pat. No. 6,333,311, which is incorporated herein by reference.

Substitutional variants or replacement variants typically contain the exchange of one amino acid for another at one or more sites within the protein. Substitutions can be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, e.g., still obtain a biological functionally equivalent protein. In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4).

Still further, it is understood that an amino acid can be substituted for another having a similar hydrophilicity value and still obtains a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

Thus, in the present invention, substitutional variants or replacements can be produced using standard mutagenesis techniques, for example, site-directed mutagenesis as disclosed in U.S. Pat. Nos. 5,220,007; 5,284,760; 5,354,670; 5,366,878; 5,389,514; 5,635,377; 5,789,166, and 6,333,311, which are incorporated herein by reference. It is envisioned that at least the N-terminal glycine amino acid residue can be replaced or substituted with any of the twenty natural occurring amino acids, for example a positively charged amino acid (arginine, lysine, or histidine), a neutral amino acid (alanine, asparagine, cysteine, glutamine, glycine, isoleucine, leucine, methionine, phenylalanine, proline, serine, threonine, tryptophan, tyrosine, valine) and/or a negatively charged amino acid (aspartic acid or glutamic acid). Still further, it is contemplated that any amino acid residue within the range of N1 to N16 can be replaced or substituted. It is envisioned that at least up to 16 of the N-terminal amino acids residues can be replaced or substituted as long as the protein retains it biological and/or functional activity, which is stimulating the production of various cytokines, (e.g., IL-18, MIP-3α, GM-CSF or IFN-γ) by inhibiting various cytokines, (e.g., IL-2, IL-4, IL-5, IL-10, and TNF-α), thus modulating and/or reducing and/or alleviating chronic or acute pain. Thus, the N-terminal lactoferrin variants of the present invention are considered functional equivalents of lactoferrin.

In terms of functional equivalents, it is well understood by the skilled artisan that, inherent in the definition of a "biologically functional equivalent" protein is the concept that there is a limit to the number of changes that may be made within a defined portion of the molecule while retaining a molecule with an acceptable level of equivalent biological activity and/or enhancing the biological activity of the lactoferrin molecule. Biologically functional equivalents are thus defined herein as those proteins in which selected amino acids (or codons) may be substituted. Functional activity is defined as the ability of lactoferrin to stimulate or inhibit various cytokines or chemokines and/or by modulating and/or reducing and/or alleviating chronic or acute pain.

Still further, the N-terminal amino acid residues can be substituted with a modified and/or unusual amino acids. A table of exemplary, but not limiting, modified and/or unusual amino acids is provided herein below.

TABLE 1

Modified and/or Unusual Amino Acids

| Abbr. | Amino Acid |
|---|---|
| Aad | 2-Aminoadipic acid |
| BAad | 3-Aminoadipic acid |
| BAla | beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| BAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| Aile | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

The presence and the relative proportion of an N-terminal lactoferrin variant (deletions and/or substitutions) in a preparation of lactoferrin (lactoferrin composition) may be determined by analyzing the N-terminal amino acid sequence by the process of Edman degradation using standard methods. A relative proportion of N-terminal lactoferrin variant comprises at least 1% of the lactoferrin composition, at least 5% of the lactoferrin composition, at least 10% of the lactoferrin composition, at least 25% of the lactoferrin composition, at least 50% of the lactoferrin composition, at least 75% of the lactoferrin composition, or about 100% of the lactoferrin composition or any range in between.

In this method, the protein is reacted with phenylisothiocyanate (PITC), which reacts with the amino acid residue at the amino terminus under basic conditions to form a phenylthiocarbamyl derivative (PTC-protein). Trifluoroacetic acid then cleaves off the first amino acid as its anilinothialinone derivative (ATZ-amino acid) and leaves the new amino terminus for the next degradation cycle.

The percentage of N-terminal lactoferrin variant may also be determined more precisely by using a dansylation reaction. Briefly, protein is dansylated using dansyl chloride reacted with the protein in alkaline conditions (pH 10). Following the dansylation, the reaction mixtures are dried to pellets, then completely hydrolyzed in 6N HCl. The proportion of N-terminal amino acids are identified by RP HPLC using an in-line fluorescence detector, by comparing with standards made up of known dansylated amino acids.

B. PHARMACEUTICAL COMPOSITIONS

The present invention is drawn to a composition comprising lactoferrin that is dispersed in a pharmaceutical carrier, which is used to treat a subject suffering from chronic or acute pain. Administration of the lactoferrin compositions according to the present invention will be via any common route, orally, parenterally or topically. Exemplary routes include, but are not limited to oral, nasal, buccal, rectal, perineum, vaginal, oro-pharyngeal cavity, topical, intradermal, subcutaneous, intramuscular, intraperitoneal, intravenous, intraarterial, intramyocardial, transendocardial, transepicardial, intrathecal, and infusion techniques. Such compositions would normally be administered as pharmaceutically acceptable compositions as described herein.

The lactoferrin that is contained in the composition of the present invention comprises lactoferrin or an N-terminal lactoferrin variant in which at least the N−1 terminal glycine residue is truncated or substituted. More specifically, the N-terminal lactoferrin variant comprises at least 1% of the composition, at least 5% of the composition, at least 10% of the composition, at least 25% of the composition, at least 50% of the composition, at least 75% of the lactoferrin composition, or about 100% of the lactoferrin composition or any range in between.

Yet further, the composition comprises lactoferrin in combination with a metal chelator dispersed in a pharmaceutical carrier. Thus, the present invention is drawn to a lactoferrin composition with or without a metal chelator that is dispersed in a pharmaceutical carrier. One of skill in the art understands that both compositions (e.g., lactoferrin alone or lactoferrin in combination with a metal chelator) are within the scope of the present invention and can be used interchangeably depending upon the type of response that is desired. It is envisioned that the addition of a metal chelator to the lactoferrin composition enhances the sequestering of metal ions and thus strengthens the immune system or enhances the effect of lactoferrin.

Metal chelators that can be used in combination with lactoferrin, include the divalent metal chelators, for example, ethylenediaminetetraacetic acid (EDTA), [ethylenebis(oxyethylenenitrilo)]tetraacetic acid (EGTA), 1,2-bis(2-aminophenoxy)ethane-N,N,N', N'-tetraacetic acid (BAPTA), hydroxyethylene diamine triacetic acid, (HEDTA) or any salts thereof. More preferably, EDTA is used in combination with lactoferrin.

Further in accordance with the present invention, the composition of the present invention suitable for administration is provided in a pharmaceutically acceptable carrier with or without an inert diluent. The carrier should be assimilable and includes liquid, semi-solid, e.g., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof.

In accordance with the present invention, the composition is combined with the carrier in any convenient and practical manner, e.g., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, e.g., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc., proteolytic enzyme inhibitors, and the like. Yet further, it is envisioned that metal chelators, for example EDTA, can also be used to stabilize the composition of the present invention. More preferably, for an orally administered composition, the stabilizer can also include antagonists to the secretion of stomach acids. Yet further, for a topically administered composition, the stabilizer can also include antagonists to skin acids.

The composition for oral administration which is combined with a semi-solid or solid carrier can be further formulated into hard or soft shell gelatin capsules, tablets, or pills. More preferably, gelatin capsules, tablets, or pills are enterically coated. Enteric coatings prevent degradation and denaturation of the composition in the stomach or upper bowel where the pH is acidic. See, e.g., U.S. Pat. No. 5,629,001. Upon reaching the small intestines, the basic pH therein dissolves the coating and permits the lactoferrin composition to be released and absorbed by specialized cells, e.g., epithelial enterocytes and Peyer's patch M cells.

In another embodiment, a powdered composition is combined with a liquid carrier such as, e.g., water or a saline solution, with or without a stabilizing agent.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Sterile injectable solutions are prepared by incorporating the lactoferrin in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Further, the composition for topical administration which is combined with a semi-solid carrier can be further formulated into a gel ointment. A preferred carrier for the formation of a gel ointment is a gel polymer. Preferred polymers that are used to manufacture a gel composition of the present invention include, but are not limited to Carbopol, carboxymethylcellulose, and Pluronic polymers. Gel polymers prevent denaturation of the composition in the open skin by serum proteases.

The amount of lactoferrin in the present invention may vary from about 1 ng to about 100 g of lactoferrin, more preferably 1 ng to 20 g per day, most preferably 0.1 g to 10 g per day. In preferred embodiments, the composition of the present invention comprises a lactoferrin concentration of about 0.1% to about 100%. The lactoferrin composition may comprise lactoferrin or an N-terminal lactoferrin variant in which at least the N−1 terminal glycine residue is truncated and/or substituted.

More preferably, the composition of the present invention also contains metal chelators, for example, but not limited to ethylenediaminetetraacetic acid (EDTA), [ethylene-bis-(oxyethylenenitrilo)]tetraacetic acid (EGTA), 1,2-bis(2-aminophenoxy)ethane-N,N,N',N'-tetraacetic acid (BAPTA), hydroxyethylene diamine triacetic acid (HEDTA) or salts thereof. The amount of the metal chelator in the composition may vary from about 1 ng to about 1 g. A preferred metal chelator is EDTA.

Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug-release capsules and the like. Some variation in dosage can occur depending on the condition of the subject being treated. The person responsible for administration can, in any event, determine the appropriate dose for the individual subject.

C. TREATMENT OF PAIN

In accordance with the present invention, the composition provided in any of the above-described pharmaceutical carriers is administered to a subject who has experienced pain which may be acute or chronic in nature. One of skill in the art can determine the therapeutically effective amount of the composition to be administered to a subject based upon several considerations, such as local effects, pharmacodynamics, absorption, metabolism, method of delivery, age, weight, disease severity and response to the therapy.

Oral administration of the composition includes oral, buccal, enteral or intragastric administration. It is also envisioned that the composition may be used as a food additive. For example, the composition is sprinkled on food or added to a liquid prior to ingestion. One of skill in the art can determine the patients who would potentially benefit from a therapeutic agent that would reduce or prevent pain or the use of concurrent or additional pain reduction therapies.

In addition to oral administration, the lactoferrin composition can also be administered parenterally or topically. Parenteral administration includes, but is not limited to intradermal, subcutaneous, intramuscular, intraperitoneal, intravenous, intraarterial, intramyocardial, transendocardial, transepicardial, intrathecal, and infusion techniques. Topical administration includes, but is not limited to topical, dermal, epidermal, oro-pharyngeal cavity, vaginal, rectal, or perineum.

Causes of acute pain include, but are not limited to pain following trauma such as a blunt or sharp injury, bullet wounds, or surgery.

Causes of chronic pain include, but are not limited to pain associated with chronic diseases such as cancer, arthritis, inflammatory disease, chronic wounds, cardiovascular accidents, disorders of the spinal chord or central nervous system, and recovery from surgery.

In further embodiments, the composition is administered in conjunction with an antacid. Thus, an antacid is administered prior or substantially simultaneously with or after oral administration of the composition. The administration of an antacid just prior or immediately following the administration of the composition may help to reduce the degree of inactivation of the lactoferrin in the digestive tract. Examples of appropriate antacids include, but are not limited to, sodium bicarbonate, magnesium oxide, magnesium hydroxide, calcium carbonate, magnesium trisilicate, magnesium carbonate and aluminum hydroxide gel.

In a preferred embodiment of the present invention, the composition is administered in an effective amount to decrease, reduce, inhibit or abrogate pain. Thus, a subject is administered a therapeutically effective amount of a lactoferrin composition so that the subject has an improvement in the parameters relating to pain including subjective measures such as pain scores and grading and objective measures including use of additional pain medications. The improvement is any observable or measurable improvement. Thus, one of skill in the art realizes that a treatment may improve the patient condition, but may not be a complete cure of the disease. The amount of lactoferrin in the composition may vary from about 1 ng to about 100 g each day. Preferably, the composition that is orally administered contains the range of 0.1 g to 10 g of lactoferrin per day.

In further embodiments, the composition of the present invention also contains metal chelators, for example, but not limited to ethylenediaminetetraacetic acid (EDTA), [ethylene-bis-(oxyethylenenitrilo)]tetraacetic acid (EGTA), 1,2-bis(2-aminophenoxy)ethane-N,N,N',N'-tetraacetic acid (BAPTA), hydroxyethylene diamine triacetic acid (HEDTA) or salts thereof. The amount of the metal chelator in the composition may vary from about 1 ng to about 1 g. A preferred metal chelator is EDTA.

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known efficacy and toxicity (if any) of the therapeutic formulations.

In specific embodiments, the composition is given in a single dose or multiple doses. The single dose may be administered daily, or multiple times a day, or multiple times a week, or monthly or multiple times a month. In a further embodiment, the lactoferrin is given in a series of doses. The series of doses may be administered daily, or multiple times a day, weekly, or multiple times a week, or monthly, or multiple times a month.

Still yet, a further embodiment is a method of enhancing a mucosal immune response in the gastrointestinal tract in a subject comprising the step of administering orally to said subject the composition of the present invention. The composition contains lactoferrin alone or in combination with a metal chelator, such as EDTA. It is envisioned that the immune response is enhanced by lactoferrin stimulating cytokines and/or chemokines. Exemplary cytokines include interleukin-18 and GM-CSF in the gastrointestinal tract, which are known to enhance immune cells or stimulate production of immune cells. For example, interleukin-18 enhances natural killer cells or T lymphocytes. In specific embodiments, interleukin-18 (IL-18) enhances CD4+, CD8+ and CD3+ cells. It is known by those of skill in the art that IL-18 is a Th1 cytokine that acts in synergy with interleukin-12 and interleukin-2 in the stimulation of lymphocyte IFN-γ production. Other cytokines or chemokines may also be enhanced for example, but not limited to IL-12, IL-1β, MIP-3α, MIP-1α or IFN-γ. Other cytokines or enzymes may be inhibited for example, but not limited to IL-2, IL-4, IL-5, IL-6, IL-10, TNF-α, or matrix metalloproteinases. It is further contemplated that lactoferrin inhibits the production of TNF-α, which inhibits cells involved in inflammation. It is also envisioned that lactoferrin stimulates interleukin-18 and a Th1 response following oral administration, which inhibits pro-inflammatory cytokines, e.g., IL-4, IL-5, IL-6, IL-8 and TNF-α.

The lactoferrin composition of the present invention can also result in inhibition of a cytokine or chemokine. The cytokines include, but are not limited to interleukin-2 (IL-2), interleukin-4 (IL-4), interleukin-5 (IL-5), interleukin-10 (IL-10), and tumor necrosis factor alpha (TNF-α). Still further, the lactoferrin composition can also inhibit the production of matrix metalloproteinases (MMPs).

In further embodiments, cytokines, for example, interleukin-18 or granulocyte/macrophage colony-stimulating factor, can stimulate the production or activity of immune cells. The immune cells include, but are not limited to T lymphocytes, natural killer cells, macrophages, dendritic cells, and polymorphonuclear cells. More specifically, the polymorphonuclear cells are neutrophils and the T lymphocytes are selected from the group consisting of CD4+, CD8+ and CD3+ T cells.

Yet further, it is envisioned that oral administration of lactoferrin in combination with a metal chelator, such as EDTA, enhances the amount of metal ion that is sequestered and therefore enhances the effectiveness of lactoferrin in enhancing the immune system.

In certain embodiments, the lactoferrin composition is administered to a subject to modulate chronic or acute pain in the subject. Modulation of pain is achieved by administering an effective amount of the composition to decrease, reduce, inhibit or abrogate pain. Specifically, it is contemplated that lactoferrin stimulates or enhances cytokine production or activity. For example, lactoferrin can enhance the production or activity of TNF-α resulting in modulation of pain, acute or chronic, in the subject.

D. COMBINATION TREATMENTS

In order to increase the effectiveness of the composition, it may be desirable to combine these compositions and methods of the invention with a known agent effective in the treatment of pain both directly and indirectly. In some embodiments, it is contemplated that a conventional therapy or agent, including but not limited to, a pharmacological therapeutic agent, a non-pharmacological pain management techniques or a combination thereof, may be combined with the composition of the present invention.

The composition of the present invention may precede, be co-current with and/or follow the other agent(s) by intervals ranging from minutes to weeks. In embodiments where the composition of the present invention, and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination. In other aspects, one or more agents may be administered within of from substantially simultaneously, about minutes to hours to days to weeks and any range derivable therein, prior to and/or after administering the composition.

Administration of the composition to a cell, tissue or organism may follow general protocols for the administration of pain therapeutics, taking into account the toxicity, if any. It is expected that the treatment cycles would be repeated as necessary. In particular embodiments, it is contemplated that various additional agents may be applied in any combination with the present invention.

A. Pharmacological Therapeutic Agents

Pharmacological therapeutic agents and methods of administration, dosages, etc. are well known to those of skill in the art (see for example, the "Physicians Desk Reference", Goodman & Gilman's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include non-steroidal anti-inflammatory drugs (NSAIDS) (e.g., aspirin, indomethacin, ibuprofen, naproxen, acetaminophen, and ketoprofen), opioid analgesics (e.g., codeine, morphine, methadone, demerol, fentanyl, oxymorphone, and levarphanol), second generation NSAIDs (e.g., COX-2 inhibitors); and anti-depressant drugs (e.g., tricyclin antidepressants, sedatives, tranquilizers, hypnotics, anti-histamines, and amphetamines).

B. Non-Pharmacological Pain Techniques

In certain aspects, a therapeutic agent may comprise a non-pharmacological pain management techniques Non-pharmacological pain management techniques are well known to those of skill in the art, and may comprise, but are not limited to acupuncture or acupressure, local anesthesia/analgesia, regional anesthesia/analgesia (e.g., epidural or spinal analgesia/anesthesia), general anesthesia/analgesia (e.g., intravenous anesthetics or opioid pump) and chiropractic. Non-pharmacological pain-reduction agents include, but are not limited to devil's, capsaicin, menthold or L-phenylalanine.

E. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Reduction in Heat-Induced Pain as Measured by Tail Flick Test in Mice

The tail flick test measures the time (max 15 s) required to elicit a radiant heat-induced tail-flick response in mice. Mice received 1000 mg/kg rhLF or placebo orally 60 minutes prior to test (N=5 per group). Oral lactoferrin treatment resulted in a statistically significant reduction in pain as measured by number of tail flicks observed. No difference in response was seen between the placebo and treated groups at time zero (FIG. 1).

Example 2

Figure 2:
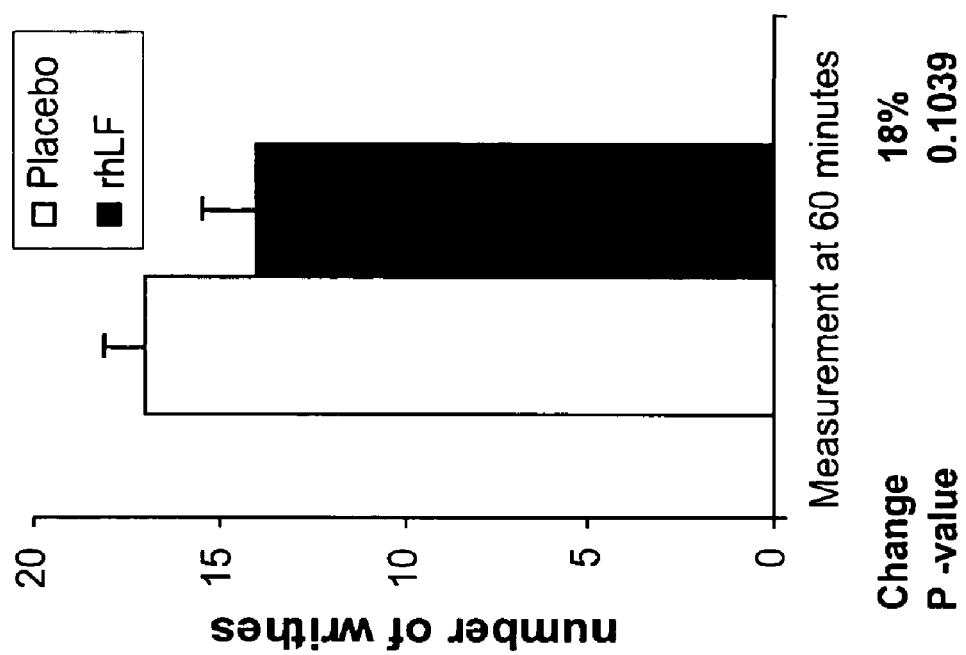
FIG. 2 shows reduction in phenylquinone-induced pain as measured by writhing test in mice.

Reduction in Phenylquinone (PQ)-Induced Pain as Measured by Writhing Test in Mice The PQ test measures the number of writhes seen during a 5-10 minute period following IP injection of phenylquinone in mice (2 mg/kg) (N=3). Mice received 1000 mg/kg rhLF or placebo orally 60 minutes prior to test (N=5 per group). Oral lactoferrin treatment resulted in a reduction in pain as measured by number of writhes observed. No difference in response was seen between the placebo and treated groups at time zero (FIG. 2).

Example 3

Reduction of Formalin Induced Pain by Recombinant Human Lactoferrin (rhLF)

Healthy mice are administered formalin by subplantar injection (5% in 0.02 ml). RhLF (20 mg/kg, 200 mg/kg), placebo or aspirin are administered by oral gavage. Frequency of hind paw licking is measured.

Example 4

Reduction of Heat Induced Tail Flick by Recombinant Human Lactoferrin (rhLF)

Healthy mice are administered rhLF (20 mg/kg or 200 mg/kg), placebo or morphine by oral gavage. The mice are then administered a focused beam of radiant heat to the middle dorsal surface of the tail. Response time to elicit the tail flick response is measured.

Example 5

Reduction of Pain in Cancer Patients

Cancer patients with severe or intractable pain are administered placebo or rhLF (3 g bid or 4.5 g bid). Reduction in pain is measured by pain scores, quality of life surveys and use of opioid analgesics.

Example 6

Reduction of Post Operative Pain

Patients recovering from major surgery requiring the use of an opioid pump are randomized to receive either placebo or rhLF (3 mg bid). Pain reduction is measured by pain scores, quality-of-life surveys and use of opioid via the pump.

Example 7

Reduction of Pain in Severe Osteoarthritis

Patients with severe intractable osteoarthritic pain are administered placebo or rhLF (3 g bid). Reduction in pain is measured by pain score, activity scores, quality of life surveys and use of analgesic medications after 7, 28 and 90 days of treatment. Improvement in joint healing is also measured by X-rays.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 5,571,691
U.S. Pat. No. 5,571,697
U.S. Pat. No. 5,571,896
U.S. Pat. No. 5,629,001
U.S. Pat. No. 6,080,559
U.S. Pat. No. 5,919,913
U.S. Pat. No. 6,228,614
U.S. Pat. No. 6,455,687
U.S. Pat. No. 6,277,817
U.S. Pat. No. 6,066,469
U.S. Pat. No. 6,100,054
U.S. Pat. No. 6,333,311

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of treating a subject suffering from pain comprising the step of administering to the subject an effective amount of a lactoferrin composition to provide a temporary improvement in pain in the subject, wherein the pain is associated with cancer and wherein said lactoferrin composition comprises an N-terminal lactoferrin variant with a deletion, substitution, or combination thereof, of from 1 to 16 N-terminal amino acid residues and the N-terminal lactoferrin variant retains the same biological function as full length lactoferrin.

2. The method of claim 1, wherein the pain associated with cancer is chronic pain.

3. The method of claim 1, wherein the N-terminal lactoferrin variant lacks at least the N-terminal glycine residue.

4. The method of claim 3, wherein said N-terminal lactoferrin variant comprises at least 1% to at least 50% w/w of the lactoferrin composition.

5. The method of claim 1, further comprising administering an antacid in conjunction with said lactoferrin composition.

6. The method of claim 1, wherein the lactoferrin composition is administered in a delayed release formulation.

7. The method of claim 6, wherein the lactoferrin composition is formulated for release in the small intestine.

8. The method of claim 6, wherein the lactoferrin composition is formulated for release in the large intestine.

9. The method of claim 1, wherein the amount of the composition that is administered comprises about 1 ng to about 100 g of lactoferrin per day.

10. The method of claim 1, wherein the amount of the composition that is administered comprises about 0.1 g to about 10 g of lactoferrin per day.

11. The method of claim 1, wherein said lactoferrin composition reduces the production or activity of pro-inflammatory cytokines.

12. The method of claim 1, wherein said lactoferrin composition enhances the production or activity of cytokines that enhance an immune response.

* * * * *